United States Patent [19]
Tsaprazis

[11] Patent Number: 4,831,362
[45] Date of Patent: May 16, 1989

[54] FAILURE DETECTION SYSTEM FOR A METALLIC DEBRIS DETECTION SYSTEM

[75] Inventor: Euripides Tsaprazis, Havertown, Pa.

[73] Assignee: Aeroquip Corporation, Jackson, Mich.

[21] Appl. No.: 863,838

[22] Filed: May 16, 1986

[51] Int. Cl.⁴ .................... G08B 29/00; G01R 35/00; G01N 27/74
[52] U.S. Cl. .................................. 340/515; 324/202; 324/204; 324/239; 340/631
[58] Field of Search ............... 324/202, 204, 226, 234, 324/236, 239, 243; 340/631, 514–516; 73/53, 61 R, 64

[56] References Cited
U.S. PATENT DOCUMENTS

| | | | |
|---|---|---|---|
| 2,942,178 | 6/1960 | Nerwin | 324/226 |
| 3,408,493 | 10/1968 | Westover et al. | 324/202 X |
| 4,084,135 | 4/1978 | Enabnit | 324/202 |
| 4,100,491 | 7/1978 | Newman et al. | 324/204 |
| 4,219,805 | 8/1980 | Magee et al. | 324/204 X |
| 4,639,666 | 1/1987 | Strosser et al. | 324/202 |
| 4,647,892 | 3/1987 | Hewitt | 324/243 |

Primary Examiner—Gerard R. Strecker
Attorney, Agent, or Firm—Lipton & Famiglio

[57] ABSTRACT

A diagnostic debris sensor operating on the inductive pulse is triggered by ferrous particles floating by or attracted to a permanent magnet within a pulse-sensing coil and the entire sensor at that, the pulse-sensing coil is equipped with a second winding for either continuous monitoring or an occasional push-to-test checking of the pulse-sensing coil.

1 Claim, 1 Drawing Sheet

FAILURE DETECTION SYSTEM FOR A METALLIC DEBRIS DETECTION SYSTEM

BACKGROUND

Devices designed for the safety of other equipment are inadequate if they can fail without either indicating their own failure or permitting a simple check test of their operating condition. The check test can be applied either continuously, or at random, depending on the respective equipment configurations and functions.

Because the subject sensor is of highly specific and specialized nature, a failure-indicating monitoring system for it must, by necessity, be of comparably unique characteristics and tailored to its respective needs.

Considering this situation, it is assumed that existing monitoring systems, if any, would not be capable of furnishing the protection for the subject sensor and its supporting equipment.

Conversely, the monitoring members devised for the subject sensor would, very likely, have few, if any, applications with other implements.

Various patents of prior and related art teach rather basic units and systems, however, without any safety or other monitoring means. Such typical teachings include, but may not be limited to, the following examples and references:

| Magee et al. | 4,219,805 | Aug. 26, 1980 |
| United Kingdom | 2 037 994 B | Apr. 13, 1983 |

None of these arrangements contains or provides for a safety feature allowing for determining the integrity of the basic sensor circuits. The latter being failure-detection components and devices, their own defects and failures, if assumed to be nonexistent, could only hasten a catastrophic result of the monitored operation and equipment.

SUMMARY OF INVENTION

This invention extends to a monitoring concept and equipment for sensors which are, in their own right, sensors expected to monitor the safe operation of often vitally important machines and engines. So long as the sensor assembly is intact, its function remains dependable. Disregarding its shell, the sensor consists of only two component parts, namely, a magnet core and a sensing coil. Because the magnet core is a rugged and passive member, only the sensing coil deserves and requires special consideration; if it becomes damaged or inoperative, the entire debris sensing, early failure detection system, is rendered useless and the to-be-protected equipment exposed to possible destruction.

The aforementioned inadequacy can be avoided through the addition of a second coil to the existing sensing coil, coupled inductively with, but otherwise isolated from each other.

Another advantage of this improvement is the now inherent capability of verifying the integrity of the circuit of the second coil thereby precluding erratic and erroneous test signals and reports.

Further advantages of this invention, per se, and over prior art will become more apparent from the following description and the accompanying drawing.

In the drawing, forming a part of this application:

DETAILED DESCRIPTION

Figure 1:
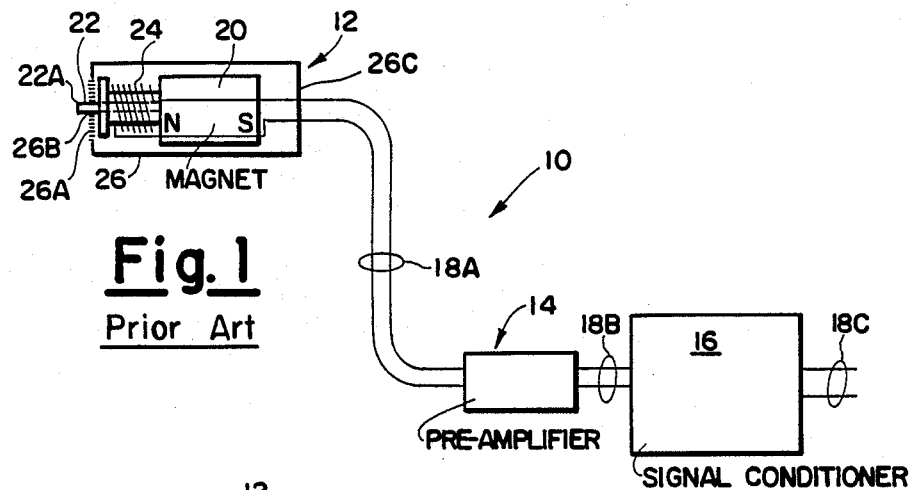
FIG. 1 is a schematic presentation of an existing sensor system and its basic accessories.

To facilitate the descriptions in the case, reference is made to an existing sensor system as shown in FIG. 1, for later comparison with the improved concept depicted in FIG. 2, whereby like reference numerals designate like or corresponding parts.

The sensing circuit 10 of the system consists of the sensor 12, a pre-amplifier 14 and a signal conditioner 16, connected through multiconductor cables 18A and 18B.

The sensor 12 consists of a permanent magnet 20 in, say, the N-S orientation shown, a substantially cylindrical, soft-iron pole piece (core) 22 extending axially from said magnet 20 and a sensing coil 24 positioned about said soft-iron pole piece 22; this entire parts assembly is enclosed within a, say, cylindrical shell 26 of a preferably nonferrous material. One of the two end faces 26A of said shell 26 has a hole 26B formed in to accommodate the face 22A of the soft-iron core 22 in at least flush surface relation with it. The shell 26 has various external threads (not shown) or flanges (not shown) formed on its outside for its installation on, to, or within vessels, hydraulic lines or comparable elements, whereby the face 26A of the shell 26 and the face 22A of the soft-iron core 22 is always exposed to the, to be monitored medium, such as lubricating oil.

The other end face 26C has connections (not shown) for the cable 18A, which is wired to a preamplifier 14. Thence, the cable 18B establishes the connection with the signal conditioner 16, whereas the cable 18C leads to a power source (not shown).

The operation of the system described above is as follows: The permanent magnet 20 generates a magnetic field in a N-S oriented circuit, flowing through the soft-iron core 22. Consequently, a ferrous particle floating past and attracted by the face 22A of said soft-iron core 22, thereby cutting across the lines of the magnetic flux, generates a voltage pulse proportional to its mass or group of masses if more than one particle is involved. This pulse is boosted through the pre-amplifier 14 and led to the signal conditioner, which, in this case, classifies the incoming amplified pulses into two (2) categories representing "total" particles greater than, say, five (5) micrograms and "large" particles greater than, say, forty (40) micrograms. Various displays and event counters can be provided to suit customer's preferences.

The foregoing equipment and operating descriptions apply to both a sensor and sensing system which are wholly intact. In the case of a defect, regardless of its location, no signals of any kind are generated, or propagated and there is no quick way of tracing, albeit finding, the fault.

Assuming that the sensor itself is the most critical system part and the most critically exposed one, and assuming further, that the sturdy permanent magnet and the equally solid soft-iron core are not likely to become damaged or inoperative, the sensing coil 24 is the member which is expected to fail and fail first compared to all other component parts.

With this situation in mind, the subject of this invention, namely, a second coil and coil winding, designated as the "diagnostics" winding, was incorporated into the sensing system.

Figure 2:
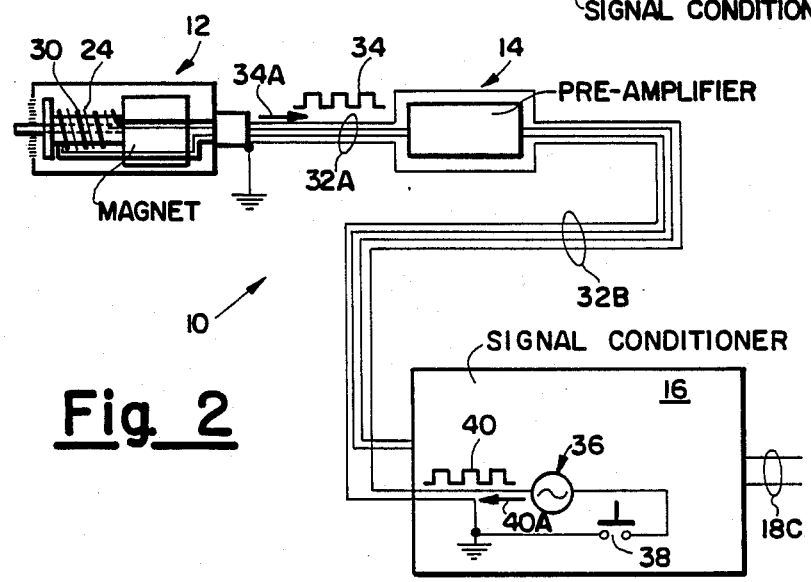
FIG. 2 illustrates, likewise schematically, the sensor in accordance with this invention, together with its circuit and the operational accessories.

This configuration is shown in FIG. 2, wherein reference numerals of parts portrayed in FIG. 1 are repeated as necessary.

The diagnostic coil with its windings 30 is applied about the sensing coil 24 and its windings; this may be accomplished with a separate coil body mounted concentrically over or next to the body of the coil 24, or by interposing the windings 30 between the windings of the coil 24, or in various other coil winding methods providing an effective inductive coupling between said two coil windings. This necessititates a four-conductor cable 32A and 32B in place of the former two-conductor cables 18A and 18B for the respective sensor 12, pre-amplifier 14 and signal conditioner 16 connections.

The basic sensor operation remains identical with that described in the forgoing. The typical pulses 34, traveling in the direction of the arrow 34A in one pair of the four-conductor cables 32A and 32B are shown, caused by passing, or captured ferrous particles, to be processed by the pre-amplifier 14 and the signal conditioner 16, respectively.

To verify the integrity of the sensor system, amounting, in essence, to a test of the main winding, i.e., coil 24 performance, a conventional signal generator 36 is added to the structure of the signal conditioner 16 and, in this example, included into the enclosure of the signal conditioner 16 as a matter of customers' convenience.

The signal generator 36 is activated by a push button 38 whenever a system test is desired, or required, causing the emission of test pulses 40 traveling in the second conductor pair of the four-conductor cables 32A and 32B and in the direction of the arrow 40A toward the diagnostic coil 30, thereby inducing in coil 24—assuming the sensing system is wholly operative—pulses 34, similar to those generated by passing or arrested ferrous particles, which are then pre-amplified and received by the signal conditioner 16. To avoid interferences, one conductor of the second four-conductor cables 32A and 32B is grounded at either conductor end 32C and 32D.

Thus the apparatus of this invention is for the testing of the integrity of a system with the sensoring and capturing, selectively, ferrous debris circulating in and with the hydraulic liquid and through the processing and displaying the signals generated by the sense and captured debris. The apparatus comprises means for the generation of signals comparable to those cause by the debris. It also includes means for the inductive coupling of the generated signals with the means for the sensing and capturing, selectively of the ferrous debris. Thus inductively introduced signals received, processed and displayed through the means for the sensing and capturing, selectively, of said ferrous debris if, and thereby verifying that, both the means are in an operating condition. The sensor is equipped with a permanent magnet, a soft-iron core magnetized by the permanent magnet and a coil to sense and capture, selectively, ferrous debris circulating in and with a liquid in a hydraulic system having amplification and signal conditioning equipment for the processing and indicating of signals generated by passing or captured ferrous debris. The sensor comprises a signal generator adapted to generate diagnostic signal pulses comparable to those generated by said ferrous debris. The sensor also includes a sensor coil having windings arranged in combination with the sensor coil so as to couple inductively with the sensor coil and thereby transmitting the generated diagnostic signal pulses for processing and displaying with and on the same system equipment negotiating the debris-cause pulses if, and thereby verifying, the entire system is in an operating condition.

It now becomes both apparent and noteworthy that in the case of a failure or defect anywhere in the sensor and/or the diagnostic system, no response will result if the push-to-test button is activated. This condition will command either immediate examination of the sensor and the diagnostic system and their repair, or the shutdown of the monitored equipment operation.

Interestingly enough, the combined sensor and diagnostic system does not only extend to the intended, periodic monitoring and testing of the sensor circuit and parts, but also to practically all other system members, including its wire connections and commercial hardware. It should, however, be borne in mind, that an indication of a sensor and diagnostic system failure does not necessarily indicate the point of failure nor the nature of the required remedial action.

The described sensing systems lend themselves to various modifications such as the amplitude of the output pulses can be set to represent a certain debris or particle size, thusly utilizing the entire available electronics components and systems involved.

It is also plausible that the herein covered system examples can be made to perform their functions for other applications, such as with industrial production, movement speed or limit indication and with security systems, and others.

It is further understood that the herein shown and described embodiments of the subject invention are but illustrative and that variations, modifications and alterations are feasible within the frame of these teachings.

What is claimed is:

1. An apparatus for testing integrity of a system for sensing and capturing, selectively, ferrous debris circulating in and with liquid in a hydraulic circuit and for proceeding and displaying signals generated by the sensed and captured debris, comprising:
   (a) means for sensing and capturing ferrous debris including substantially cylindrical magnetic means for generating a magnetic field to attract and capture said ferrous debris on an end face of said cylindrical magnetic means and first inductive coil positioned about said magnetic means and coupled sensing means adapted to measure changes in the electrical voltage induced in said first coil by changes in the magnetic field caused by the accumulation of ferrous debris.
   (b) means for generating diagnostic signals to produce electrical voltage changes in said first coil comparable to the electrical voltage changes in said first coil caused by the accumulation of ferrous debris by said magnetic means;
   (c) a second coil, positioned about said magnetic means, located in close proximity to said first coil and selectively connectable to said diagnostic signal generating means for the purpose of inductively coupling said generated diagnostic signals to said first coil;
   wherein said generated diagnostic signal are electrically coupled from said second coil to said first coil to induce electrical voltage changes in said first coil and wherein said sensing means coupled with said first coil provides an indication of the integrity of said sensing and capturing system.

* * * * *

UNITED STATES PATENT AND TRADEMARK OFFICE
CERTIFICATE OF CORRECTION

PATENT NO. : 4,831,362
DATED : May 16, 1989
INVENTOR(S) : Euripides Tsaprazis

It is certified that error appears in the above-identified patent and that said Letters Patent is hereby corrected as shown below:

Claim 1, line 10 after the word "and" the word "a" should be inserted.

Claim 1, line 12 before the first word "sensing" the word "with" should be inserted.

Claim 1, line 27 the word "signal" should have an "s" on the end making this word plural.

Signed and Sealed this

Twenty-second Day of May, 1990

Attest:

HARRY F. MANBECK, JR.

*Attesting Officer*    *Commissioner of Patents and Trademarks*